US012533015B2

(12) United States Patent
Schwarz

(10) Patent No.: US 12,533,015 B2
(45) Date of Patent: Jan. 27, 2026

(54) DATA TRANSMISSION VIA ROTATING INTERFACES IN ENDOSCOPIC APPLICATIONS

(71) Applicant: KARL STORZ SE & Co. KG, Tuttlingen (DE)

(72) Inventor: Peter Schwarz, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 390 days.

(21) Appl. No.: 18/066,097

(22) Filed: Dec. 14, 2022

(65) Prior Publication Data

US 2023/0190081 A1 Jun. 22, 2023

(30) Foreign Application Priority Data

Dec. 22, 2021 (DE) ..................... 10 2021 134 433.6

(51) Int. Cl.
*A61B 1/00* (2006.01)

(52) U.S. Cl.
CPC ...... *A61B 1/00181* (2013.01); *A61B 1/00177* (2013.01)

(58) Field of Classification Search
CPC ............ A61B 1/00177; A61B 1/00181; A61B 1/00114; A61B 1/00124
See application file for complete search history.

(56) References Cited

U.S. PATENT DOCUMENTS 5,394,187 A * 2/1995 Shipp .................. H04N 13/211 348/E13.059
7,471,310 B2 12/2008 Amling et al.
(Continued)

FOREIGN PATENT DOCUMENTS

DE 2938882 C2 4/1980
DE 102007001751 A1 7/2008
(Continued)

OTHER PUBLICATIONS

Texas Instruments, DS90UB953-Q1 FPD-Link III 4. 16-Gbps Serializer With CSI-2 Interface for 2.3MP/60fps Cameras, RADAR, and Other Sensors, Product information, 2018, pp. 1-89, Texas Instruments, Dallas, USA.
(Continued)

*Primary Examiner* — Aaron B Fairchild
(74) *Attorney, Agent, or Firm* — David N. Villalpando; Jacqueline Cohen

(57) ABSTRACT

A medical scope (10) comprises an objective (42) forming an image of an object; an image sensor (44) capturing the image formed by the objective (42) and providing an image signal representing the captured image; a serializer (50) comprising a two-conductor first interface (52) and a multi-conductor second interface (54) connected to the image sensor (44); a first sliding contact (71) and a second sliding contact (72) connected to the two-conductor first interface (52) of the serializer (50); a third sliding contact (73) in electrically conductive contact to the first sliding contact (71) and a fourth sliding contact (74) in electrically conductive contact to the second sliding contact (72). The at least two of the first sliding contact (71), the second sliding contact (72), the third sliding contact (73) and the fourth sliding contact (74) are coaxial.

11 Claims, 4 Drawing Sheets

(56) References Cited

U.S. PATENT DOCUMENTS

| | | | | |
|---|---|---|---|---|
| 8,926,336 | B2 | 1/2015 | Göbel et al. | |
| 2005/0154262 | A1* | 7/2005 | Banik | A61B 1/128 600/179 |
| 2006/0114986 | A1 | 6/2006 | Knapp, II et al. | |
| 2006/0287576 | A1 | 12/2006 | Tsuji et al. | |
| 2008/0009675 | A1* | 1/2008 | Kura | A61B 1/005 600/128 |
| 2008/0300456 | A1 | 12/2008 | Irion et al. | |
| 2009/0027490 | A1 | 1/2009 | Hirai et al. | |
| 2010/0022829 | A1 | 1/2010 | Irion et al. | |
| 2012/0100729 | A1 | 4/2012 | Edidin et al. | |
| 2012/0209061 | A1 | 8/2012 | Kato | |
| 2015/0094536 | A1 | 4/2015 | Wieth et al. | |
| 2015/0305602 | A1 | 10/2015 | Gal et al. | |
| 2015/0359420 | A1 | 12/2015 | Hatase et al. | |
| 2016/0073855 | A1 | 3/2016 | Farr et al. | |
| 2020/0146539 | A1 | 5/2020 | Hirono | |

FOREIGN PATENT DOCUMENTS

| | | | |
|---|---|---|---|
| DE | 102013102309 | A1 | 9/2013 |
| EP | 3769658 | A1 | 1/2021 |
| WO | 2008018256 | A1 | 2/2008 |
| WO | 2024194856 | A1 | 9/2024 |

OTHER PUBLICATIONS

Obermeier, DPMA Search Report (German Language), Sep. 8, 2022, pp. 1-8, German Patent Office, Munich.
Doyle, A., Extended European Search Report, Jul. 6, 2023, pp. 1-9, European Patent Office, Munich.

* cited by examiner

DATA TRANSMISSION VIA ROTATING INTERFACES IN ENDOSCOPIC APPLICATIONS

CROSS REFERENCE TO RELATED APPLICATIONS

This application claims priority to German Patent Application No. 102021134433.6, filed Dec. 22, 2021, and entitled, "Medical Scope," which is incorporated herein by reference.

FIELD OF THE INVENTION

The present invention refers to a medical scope, more particularly a medical endoscope or exoscope or a surgical microscope. In particular, the present invention refers to the transfer of power and a control signal to an image sensor and the transfer of an image signal from the image sensor to a camera control unit, primarily when the image sensor is located at the distal end of the shaft of the medical scope.

BACKGROUND OF THE INVENTION

An image sensor capturing images requires electrical power, and usually additionally requires a control signal to control the clock, the electronic shutter, the sensitivity and/or other parameters that the control signal provides to the image sensor. An image signal representing images captured by the image sensor is provided by the image sensor and is transferred to a camera control unit or another device processing, analyzing, storing and/or forwarding the image signal to a display. The transfer of power, a control signal, and an image signal can be challenging, in particular when the image sensor is located in a small volume distal end of a medical scope and the transfer needs to be along a long and thin shaft. Pivotability or rotatability of the image sensor further increases the technical challenge.

An object of the present invention is to provide an improved medical scope.

BRIEF DESCRIPTION OF THE INVENTION

A medical scope comprises an objective producing an image of an object, an image sensor capturing the image produced by the objective and providing an image signal representing the captured image, a serializer comprising a two-conductor first interface and a multi-conductor second interface connected to the image sensor, a first sliding contact and a second sliding contact connected to the two-conductor first interface of the serializer, a third sliding contact in electrically conductive contact to the first sliding contact and a fourth sliding contact in electrically conductive contact to the second sliding contact, wherein at least two of the first sliding contact, the second sliding contact, the third sliding contact and the fourth sliding contact are coaxial.

A medical scope comprises an objective producing an image of an object, an image sensor capturing the image produced by the objective and providing an image signal representing the captured image, a serializer comprising a two-conductor first interface and a multi-conductor second interface connected to the image sensor, a deserializer comprising a two-conductor first interface coupled to the two-conductor first interface of the serializer by a pair of conductors and a multi-conductor second interface coupled to a camera control unit or to a connector which can be connected to a camera control unit.

The medical scope may be an endoscope or an exoscope or a surgical microscope. The objective comprises one or more lenses. The objective can provide a fixed focal length or a variable focal length. The objective and the image sensor can be in a fixed-focus configuration. As an alternative, the objective can be controllable to produce sharp images of objects within a range of distances.

The serializer is configured to receive electrical power and optionally also a control signal via its two-conductor (or two-wire or two-core) first interface and provide the power and optionally the control signal at two or more conductors of the multi-conductor (or multi-wire or multi-core) second interface and to receive the image signal provided by the image sensor via two or more conductors of the multi-conductor second interface and transmit the image signal via the two-conductor first interface.

The deserializer is configured to receive electrical power and optionally also a control signal from a camera control unit or any other device via two or more conductors of its multi-conductor second interface and to transmit the power and optionally also the control signal via its two-conductor first interface to the two-conductor first interface of the serializer. Furthermore, the deserializer is configured to receive via its two-conductor first interface the image signal and to transmit the image signal via its multi-conductor second interface to a camera control unit.

According to the invention, both power and optionally the control signal and an image signal are transferred (in opposite directions) via the same two-conductor connection. This two-conductor connection requires less space than a multi-conductor connection and facilitates new technical solutions to challenges like pivotability or rotatability of the image sensor or separability of components of the medical scope.

A medical scope comprising a deserializer as it is described herein in particular further comprises a first sliding contact and a second sliding contact connected to the two-conductor first interface of the serializer and a third sliding contact and a fourth sliding contact coupled to the two-conductor first interface of the deserializer, wherein the first sliding contact is in electrically conductive contact to the third sliding contact and the second sliding contact is in electrically conductive contact to the fourth sliding contact, and wherein at least two of the first sliding contact, the second sliding contact, the third sliding contact and the fourth sliding contact are coaxial.

Each one of the first and second sliding contacts is connected to a respective conductor of the two-conductor first interface of the serializer. Each one of the third and fourth sliding contacts is (directly or indirectly) coupled to a respective conductor of the two-conductor first interface of the deserializer.

In particular, at least two of the first sliding contact, the second sliding contact, the third sliding contact and the fourth sliding contact are shaped as sections of surfaces of cylinders or cones or other geometrical objects which provide rotational symmetry with respect to the same axis of symmetry. In particular, each of the first sliding contact and the second sliding contact are annular sections of cylinder surfaces rotationally symmetric with respect to the same axis of symmetry, wherein the third and fourth sliding contacts can be coaxial as well or can provide other geometry.

A medical scope as it is described herein in particular further comprises an image sensor unit including the image sensor, the serializer, the first sliding contact and the second sliding contact and a shaft with a distal end region including the third sliding contact and the fourth sliding contact.

The image sensor unit can be pivotable or rotatable about an axis of rotation relative to the shaft. This axis of rotation is in particular identical to the axis of symmetry of at least two of the first sliding contact, the second sliding contact, the third sliding contact and the fourth sliding contact.

In a medical scope as it is described herein, the first sliding contact and the second sliding contact are in particular part of a first coaxial plug connector, wherein the third sliding contact and the fourth sliding contact are part of a second coaxial plug connector complementary to the first coaxial plug connector.

The first coaxial plug connector is in particular part of or mechanically integrated with the image sensor unit. The second coaxial plug connector is in particular part of or mechanically integrated with the distal end region of the shaft. The complementary coaxial plug connectors can allow the image sensor unit to be separable from the shaft. Separability can facilitate cleaning and sterilization as well as replacement of the image sensor unit in case of failure or malfunction. Furthermore, the image sensor unit can be easily replaced if other characteristics are required, for example regarding resolution, sensitivity, field of view or spectral sensitivity.

In a medical scope as it is described herein, an axis of symmetry of the coaxial sliding contacts is in particular parallel to the viewing direction of the image sensor unit.

In particular in case of a stereoscopic medical scope this allows the stereo base to be rotated and, in particular, to be held horizontal.

In a medical scope as it is described herein, the axis of symmetry of the coaxial sliding contact is in particular orthogonal to the viewing direction of the image sensor unit and orthogonal to the longitudinal axis of the distal end region of the shaft.

Two axes or directions are orthogonal if they include an angle between 80 degrees and 100 degrees or between 85 degrees and 95 degrees or if the included angle is essentially or exactly 90 degrees.

This orientation of the axis of symmetry allows a largely free rotation of the viewing direction.

A medical scope as it is described herein in particular further comprises a fifth sliding contact connected to the third sliding contact, a sixth sliding contact connected to the fourth sliding contact, a seventh sliding contact in electrically conductive contact to the fifth sliding contact and an eighth sliding contact in electrically conductive contact to the sixth sliding contact, wherein at least two of the fifth sliding contact, the sixth sliding contact, the seventh sliding contact and the eighth sliding contact are coaxial.

In particular, a pair of conductors connects the fifth sliding contact to the third sliding contact and the sixth sliding contact to the fourth sliding contact, respectively. In particular, another pair of conductors connects the seventh sliding contact and the eighth sliding contact to the two-conductor first interface of the deserializer.

In particular, at least two of the fifth sliding contact, the sixth sliding contact, the seventh sliding contact and the eighth sliding contact are shaped as sections of surfaces of cylinders or cones or other geometrical objects which provide rotational symmetry with respect to the same axis of symmetry. In particular, each of the fifth sliding contact and the sixth sliding contact are annular sections of cylinder surfaces rotationally symmetric with respect to the same axis of symmetry, wherein the third and fourth sliding contacts can be coaxial as well or can provide other geometry.

The image sensor or, if applicable, the image sensor unit or part of the image sensor unit can be pivotable or rotatable about a second axis of rotation relative to the shaft. This second axis of rotation is in particular identical to the axis of symmetry of at least two of the fifth sliding contact, the sixth sliding contact, the seventh sliding contact and the eighth sliding contact.

In particular, the fifth sliding contact and the sixth sliding contact are part of a third coaxial plug connector and the seventh sliding contact and the eighth sliding contact are part of the fourth coaxial plug connector complementary to the third coaxial plug connector. In this case, the fifth, sixth, seventh and eighth sliding contacts can provide a second separable plug connection and/or a second axis of rotation the image sensor or the image sensor unit can be rotated or pivoted about.

In a medical scope as it is described herein, an axis of symmetry of at least two of the first sliding contact, the second sliding contact, the third sliding contact and the fourth sliding contact and an axis of symmetry of at least two of the fifth sliding contact, the sixth sliding contact, the seventh sliding contact and the eighth sliding contact enclose an angle greater than zero.

In particular, the axes of symmetry enclose an angle between 70 degrees and 110 degrees or between 80 degrees and 100 degrees or essentially or exactly 90 degrees.

In particular in case of a stereoscopic medical scope, these two orthogonal axes of symmetry can be axes of rotation and can facilitate a free or largely free rotation of the viewing direction while the stereo base can be held horizontal continuously.

In a medical scope as it is described herein, the serializer and the deserializer in particular comply with the CSI camera serial interface specification of the MIPI mobile industry processor interface alliance.

The CSI specification of the MIPI alliance provides a well-established, verified and robust standard ensuring high performance and reliability.

The serializer can be integrated with the image sensor. In particular the serializer and the image sensor can be located on or in the same die, chip or device. The deserializer can be located close to or can even be partially or fully integrated with a camera control unit, wherein the camera control unit can be partially or fully integrated with the medical scope or can be a separate device. When the deserializer is part of the medical scope it is in particular located in or at the proximal end of the medical scope.

In a medical scope as it is described herein, the serializer and the deserializer are in particular FPD modules.

For example, each of the serializer and the deserializer is or comprises a device DS90UB953-Q1 by Texas Instruments or a similar device.

A medical scope as it is described herein is in particular a stereoscopic endoscope or exoscope or surgical microscope capturing a first image to be displayed to the left eye of medical personnel and a second image to be displayed to the right eye of the medical personnel. The first and second images can be captured simultaneously or almost simultaneously, for example alternatingly.

BRIEF DESCRIPTION OF THE DRAWINGS

Embodiments will be described below with reference to the enclosed figures.

DETAILED DESCRIPTION OF THE INVENTION

Figure 1:
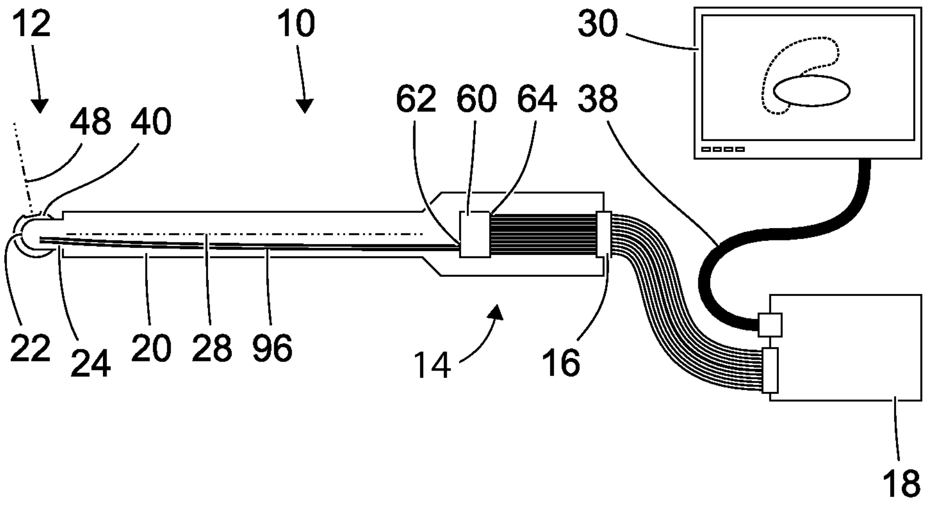
FIG. 1 shows a schematic representation of an endoscope.

FIG. 1 shows a schematic representation of an endoscope 10 as an example of a medical scope. The endoscope 10 includes a distal end 12 to be inserted into a natural or artificial cavity in the body of a human or animal patient and a proximal end 14. The proximal end 14 can provide a user interface, for example one or more buttons, sliders, rotatable knobs which can be manipulated by one or more fingers and control mechanical, electrical, hydraulic, pneumatic or other functions of the endoscope. Furthermore, the proximal end 14 of the endoscope 10 includes a connector 16 which can be connected to a camera control unit 18 by a cable.

The endoscope 10 includes a shaft 20 with a distal end 22, a distal end region 24, and a longitudinal axis 28. The longitudinal axis 28 of the shaft is generally defined as the line formed by the center points of all cross sections of the shaft 20.

In the example shown in FIG. 1, the shaft 20 is straight and rigid, however, in other embodiments some or all of the shaft 20 may be flexible.

An image sensor unit 40 is connected to the distal end region 24 of the shaft 20. The image sensor unit 40 includes one or more objectives or lenses producing one or more images and one or more image sensors capturing the image or the images. The arrangement of at least one objective and the corresponding image sensor defines the viewing direction 48 of the image sensor unit 40. In the example shown, the image sensor unit 40 and the viewing direction 48 can be pivoted about an axis orthogonal to the drawing plane of FIG. 1.

From a functional point of view, the image sensor unit 40 can be seen as a part of the shaft 20, being the very distal end 12 of the endoscope 10. From the designed perspective or from the perspective of mechanical structure, the shaft 20 and the image sensor unit 40 are two modules or members mechanically coupled together. More details of the distal end region 24 of the shaft 20 and the image sensor unit 40 are described with reference to FIGS. 4 through 7.

In the shaft 20, a pair of conductors 96, such as conductive wires or a flexible circuit board, connects a serializer located in the image sensor unit 40 to a deserializer 60 located in the proximal end 14 of the endoscope 10. The deserializer 60 provides a two-conductor first interface 62 connected to a corresponding two-conductor first interface of the serializer in the image sensor unit 40 and a multi-conductor second interface 64 connected to the camera control unit 18 via the connector 16.

The deserializer 60 receives at its multi-conductor second interface 64 electrical power and a control signal from the camera control unit 18 and transmits electrical power and the control signal via its two-conductor first interface 62 and the pair of conductors 96 to the serializer in the image sensor unit 40. Furthermore, the deserializer 60 receives at its two-conductor first interface 62 an image signal transmitted by the serializer in the image sensor unit 40 via the pair of conductors 96. The deserializer 60 forwards this image signal through its multi-conductor second interface 64 and via the connector 16 to the camera control unit 18.

Thus, both electrical power and the control signal are provided to the image sensor unit 40 and the image signal is received from the image sensor unit 40 via the same single pair of conductors 96.

The camera control unit provides electrical power and the control signal, receives and processes the image signal and provides the processed image signal to a display device 30 connected to the camera control unit 18 by a cable 38.

Figure 2:
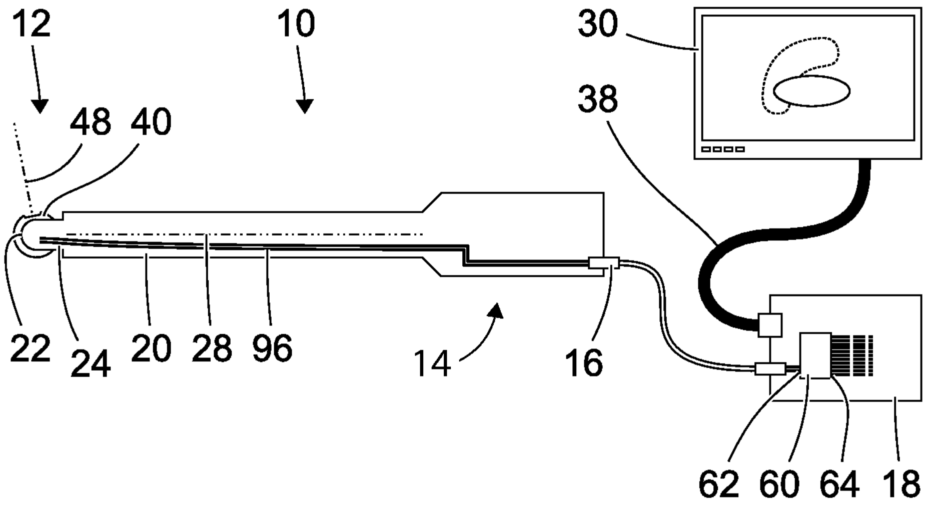
FIG. 2 shows a schematic representation of another endoscope.

FIG. 2 shows a schematic representation of another endoscope 10 similar to the endoscope described above with reference to FIG. 1 with respect to many features, characteristics and functions. Differences between the endoscope 10 shown in FIG. 2 and the endoscope described above with reference to FIG. 1 are described below.

The endoscope 10 shown in FIG. 2 does not comprise a deserializer. Rather, the camera control unit 18 comprises a deserializer 60 similar to the deserializer of the endoscope described above with reference to FIG. 1. Thus, the connector 16 at the proximal end 14 of the endoscope 10 and the cable connecting the connector 16 to the camera control unit 18 can be of the two-conductor type. The two-conductor first interface 62 of the deserializer 60 is connected to the connector 16 of the endoscope 10 by a cable. The multi-conductor second interface 64 of the deserializer 60 is connected to further components of the deserializer 60 which are not shown in FIG. 2.

Figure 3:
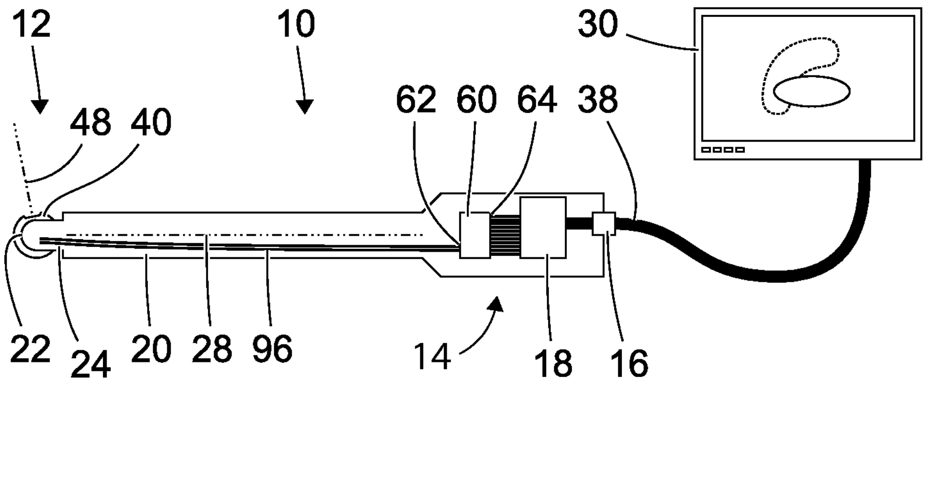
FIG. 3 shows a schematic representation of another endoscope.

FIG. 3 shows a schematic representation of another endoscope 10 similar to the endoscope described above with reference to FIG. 1 with respect to many features, characteristics and functions. Differences between the endoscope 10 shown in FIG. 3 and the endoscope described above with reference to FIG. 1 are described below.

In the example shown in FIG. 3, the camera control unit 18 is integrated into the proximal end 14 of the endoscope 10. The endoscope 10 provides a fully processed and conditioned image signal for a display which can be directly coupled to the connector 16. In this case, the endoscope 10 may receive electrical power from the display via the connector 16.

Figure 4:
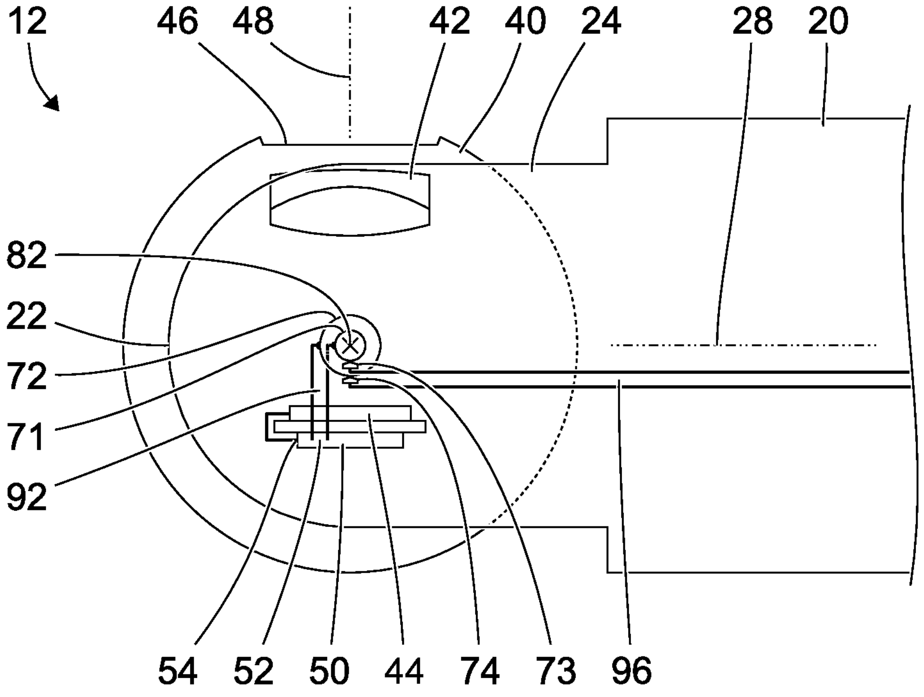
FIG. 4 shows a magnified schematic representation of the distal end region of the shaft of one of the endoscopes shown in FIGS. 1 through 3.

FIG. 4 shows an enlarged schematic representation of the shaft 20, the distal end region 24 of the shaft and the image sensor unit 40 forming the very distal end 12 of one of the endoscopes described above with reference to FIGS. 1 through 3. The distal end region 24 of the shaft 20 is bifurcated. In the viewing direction of FIG. 4, one prong is in front of the image sensor unit 40, and the other prong is behind the image sensor unit 40. The contour of the image sensor unit 40 is shown in a broken line where it is actually hidden behind one prong of the distal end region 24 of the shaft 20. The essentially circular contour of the image sensor unit 40 is visible.

A flat area 46 of the outer surface of the image sensor unit 40 is formed by a light entrance window. In the example shown in FIG. 1, the flat area 46 provides the only deviation from a circular contour.

In FIG. 4, components located inside the visible prong of the distal end region 24 or inside the image sensor unit 40 and, thus, actually invisible in reality, are shown. In particular, the image sensor unit 40 comprises an objective 42 producing a real image. Capturing the real image produced by the objective 42 and providing an image signal representing the captured image is image sensor 44. The arrangement of the objective 42 and the image sensor 44 constitutes the viewing direction 48.

Furthermore, the image sensor unit 40 comprises a serializer 50 with a two-conductor first interface 52 and a multi-conductor second interface 54. The multi-conductor second interface 54 is connected to the image sensor 44 by a corresponding number of parallel conductors. A pair of conductors 92 connects the two-conductor first interface 52 of the serializer 50 to a first sliding contact 71 and a second sliding contact 72, respectively. Each of the first sliding contact 71 and the second sliding contact 72 is cylindrical with a circular cross section and identical cylinder axes 82 orthogonal to the drawing plane of FIG. 4. Thus, both the first and the second sliding contact 71, 72 provide rotational symmetry with respect to the same axis of symmetry 82.

The first and second sliding contacts 71, 72 are arranged coaxial are rigidly connected to or integral with other components of the image sensor unit 40, in particular with the housing of the image sensor unit 40. The image sensor unit 40 including the first and second sliding contacts 71, 72 can be rotated about the axis 82 of symmetry of the first and second sliding contacts 71, 72.

As will be described in more detail in FIG. 5, the first and second sliding contacts 71, 72 of the image sensor unit 40 protrude from the overall outer surface of the image sensor unit 40 and engage in a recess in the prong of the distal end region 24. At the inner surface of their recess, one or more third sliding contacts 73 in electrically conductive contact to the first sliding contact 71 and one or more fourth sliding contacts 74 in electrically conductive contact to the second sliding contact 72 are arranged. The pair of conductors 96 connects the one or more third sliding contacts 73 and the one or more fourth sliding contacts 74, respectively, to the two-conductor first interface 62 of the deserializer 60 (cf. FIGS. 1 through 3).

As a result, the image sensor 44 is connected to the camera control unit 18 by the serializer 50, the pair of conductors 92, the first and second sliding contacts 71, 72 rigidly connected to the rest of the image sensor unit 40, the third and fourth sliding contacts 73, 74 rigidly connected to the distal end region 24 of the shaft 20, the pair of conductors 96 and the deserializer 60 shown in FIGS. 1 through 3. While electrical power and the control signal (from the camera control unit 18 to the image sensor 44) and the image signal representing the captured image (from the image sensor 44 to the camera control unit 18) are usually transferred via different conductors or sets of conductors between the camera control unit 18 and the deserializer 60 and between the serializer 50 and the image sensor 44, both electrical power and the control signal and the image signal are transferred via the same pair of conductors 92, via one coaxial arrangement of sliding contacts 71, 72, 73, 74 and again a pair of conductors 96. Thus, the room or space required for the transfer of electrical power, the control signal and the image signal, in particular between the distal end region 24 of the shaft 20 and the image sensor unit 40 is considerably reduced.

Figure 5:
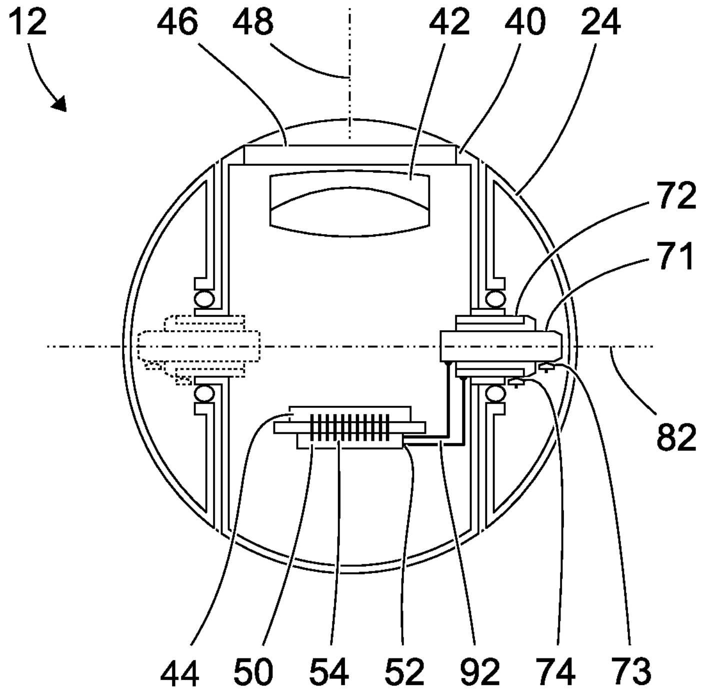
FIG. 5 shows another schematic representation of the distal end region of FIG. 4.

FIG. 5 shows another schematic representation of the endoscope's distal end 12 described above with reference to FIG. 4. The drawing plane of FIG. 5 is orthogonal to the drawing plane of FIG. 4 and orthogonal to the longitudinal axis 28 of the shaft 20 (cf. FIGS. 1 through 4) and comprises the axis of symmetry 82 of the first and second sliding contacts 71, 72 about which the image sensor unit 40 can be rotated. Again, both the contours of the prongs forming the distal end region 24 of the shaft and the contour of the image sensor unit 40 and components located inside the prongs forming the distal end region 24 of the shaft 20 and components located inside the image sensor unit 40 are shown in FIG. 5.

The first sliding contact 71 is formed by a circular cylindrical and electrically conductive rod. The second sliding contact 72 is formed by an electrically conductive tube arranged coaxial to the rod. Isolating structures (for example made from ceramics or plastics) electrically insulate the first and second sliding contacts 71, 72 from each other and optionally also from the housing of the image sensor unit 40. A sealing ring can prevent entry of a fluid or other debris into the recess in which the third and fourth sliding contacts 73, 74 are arranged.

In the example shown in FIGS. 4 and 5, the image sensor 44 and the serializer 50 are distinct (and different) components arranged at opposite sides of a circuit board. As an alternative, the image sensor 44 and the serializer 50 can be arranged at the same side of a circuit board or in any other geometrical configuration or can be integrated in one chip or even in one die.

In the example shown in FIGS. 4 and 5, the first and second sliding contacts 71, 72 protrude from the housing of the image sensor unit 40 and engage into a recess in the distal end region 24 of the shaft where the third and fourth sliding contacts 73, 74 are arranged. As an alternative, the third and fourth sliding contacts 73, 74 can protrude from the distal end region 24 and engage into a recess in the image sensor unit 40.

In the example shown in FIGS. 4 and 5, only the first and second sliding contacts 71, 72 provide rotational symmetry with respect to the axis 82. As an alternative, both the first and second sliding contacts 71, 72 and the third and fourth sliding contacts 73, 74 can provide rotational symmetry with respect to the axis 82. As a further alternative, only the third and fourth sliding contacts 73, 74 provide rotational symmetry with respect to the axis 82. As a further alternative, one of the first and third sliding contacts 71, 73 and one of the second and fourth sliding contacts 72, 74 provides rotational symmetry with respect to the axis 82.

In the example shown in FIGS. 4 and 5, only one coaxial connector formed by the first, second, third and fourth sliding contacts 71, 72, 73, 74 is provided. As an alternative, a second coaxial connector providing rotational symmetry with respect to the same axis 82 can be provided as indicated by broken lines.

Figure 6:
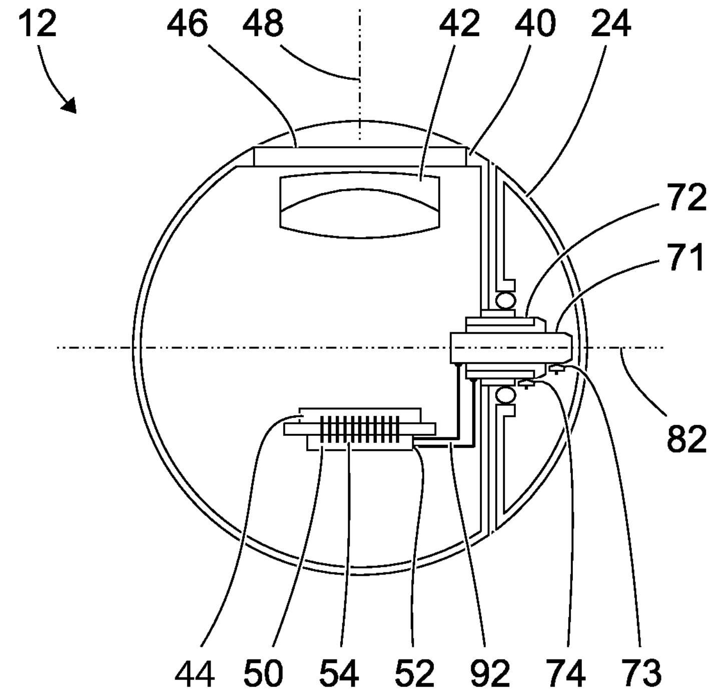
FIG. 6 shows a schematic representation of another distal end region.

FIG. 6 shows a schematic representation of a distal end 12 of an endoscope similar to the endoscopes described above with reference to FIGS. 1 through 5 with respect to many features, characteristics and functions. Differences between the distal end 12 shown in FIG. 6 and the distal end described above with reference to FIGS. 4 and 5 are described below. The way the distal end 12 of the endoscope is displayed in FIG. 6 is similar to FIG. 5.

The distal end 12 displayed in FIG. 6 differs from the distal end described above with reference to FIGS. 4 and 5 in that the distal end region 24 of the shaft is not bifurcated. Rather, the distal end region is formed by only one rod like structure with a cross section similar to a circular segment. As a consequence, the mechanical connection between the distal end region 24 and the image sensor unit 40 can be non-destructively separable. In particular, the first and second sliding contacts 71, 72 are part of a first coaxial plug connector rigidly connected to the image sensor unit 40, and the third and fourth sliding contacts 73, 74 are parts of a coaxial plug connector integrated into the distal end region 24 of the shaft. The image sensor unit 40 can be pulled off from the distal end region 24 in a direction parallel to the axis of symmetry 82 of at least two of the sliding contacts 71, 72, 73, 74. This can facilitate disassembly before the endoscope is cleaned, replacement of a faulty image sensor unit 40 or replacement of an image sensor unit 40 by an image sensor unit with different characteristics.

Figure 7:
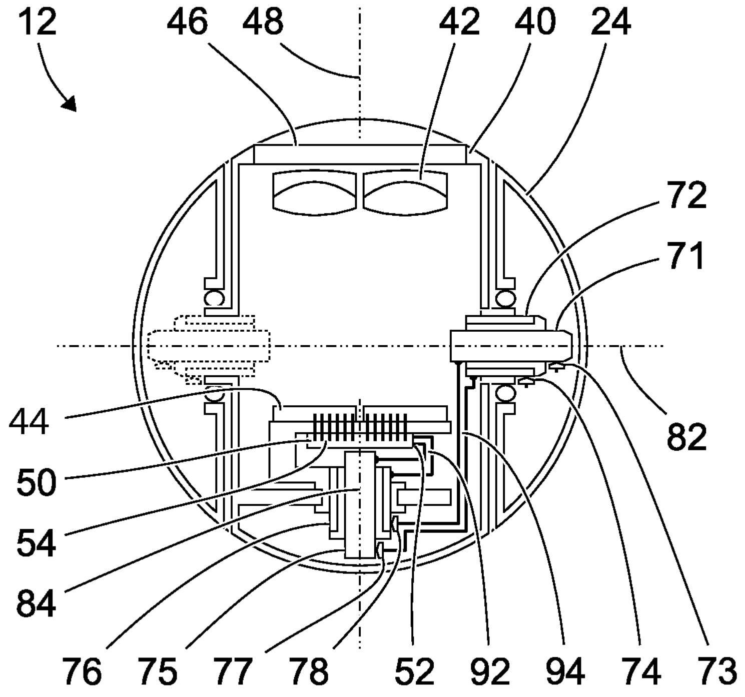
FIG. 7 shows a schematic representation of another distal end region.

FIG. 7 shows a schematic representation of a distal end 12 of an endoscope similar to the endoscopes described above with reference to FIGS. 1 through 5 with respect to many features, characteristics and functions. Differences between the distal end 12 displayed in FIG. 7 and the distal end described above with reference to FIGS. 4 and 5 are described below. The way the distal end 12 is shown in FIG. 7 is similar to FIGS. 5 and 6.

There are two main differences between the distal end 12 shown in FIG. 7 and the distal end described above with reference to FIGS. 4 and 5. One main difference regards stereoscopic imaging; the other main difference regards rotatability about a second axis. Although rotatability about a second axis is particularly relevant in case of stereoscopic imaging, both main differences are independent from one each other to a large extent. Stereoscopic imaging can be realized without rotatability about a second axis, and rotatability about a second axis can be realized in a monocular endoscope as well.

Regarding stereoscopic imaging, two objectives 42 and two image sensors 44 are provided capturing two images from slightly different positions. In the example shown in FIG. 7, both image sensors 44 are connected to two distinct multi-conductor second interfaces 54 of the same serializer 50 or to partly or entirely distinct parts of the same multi-conductor second interface 54 of the same serializer 50. As an alternative, two serializers 50 are provided and the multi-conductor second interface 54 of each of the serializers 50 is connected to a respective one of the image sensors 44.

Regarding rotatability about the second axis, the entire arrangement of the two objectives 42 and the two image sensors 44 is rotatable about a second axis 84 orthogonal to the first axis 82 and parallel to or identical with the viewing direction 48 of the image sensor unit 40. The second axis 84 can be pivoted about the first axis 82 together with the image sensor unit 40. In the configuration shown in FIG. 7, the drawing plane comprises both the second axis 84 and the viewing direction 48, and the second axis 84 and the viewing direction 48 are orthogonal to the longitudinal axis of the shaft. In particular, the image sensor unit 40 comprises a housing pivotable about the first axis 82, wherein the arrangement formed by the objectives 42, the image sensors 44 and the serializer 50 can be rotated about the second axis 84 within the housing of the image sensor unit 40.

An arrangement of a fifth sliding contact 75, a sixth sliding contact 76, a seventh sliding contact 77 and an eighth sliding contact 78 is similar to the arrangement of the first sliding contact 71, the second sliding contact 72, the third sliding contact 73 and the fourth sliding contact 74. The fifth, sixth, seventh and eighth sliding contact 75, 76, 77, 78 form a two-conductor coaxial connector coupling the pair of conductors 92 coupled to the two-conductor first interface 52 of the serializer 50 and a pair of conductors 94. The other end of the pair of conductors 94 is connected to the first and second sliding contacts 71, 72. Rotational symmetry of at least one of the fifth sliding contact 75 and the seventh sliding contact 77 and of at least one of the sixth sliding contact 76 and the eighth sliding contact 78 about the second axis 84 guarantees a continuous two-conductor connection of the two-conductor first interface 52 of the serializer 50 to the pair of conductors 94. In total, the sliding contacts 71, 72, 73, 74, 75, 76, 77, 78 and their symmetries about the first axis 82 and the second axis 84, respectively, facilitate that the image sensor unit 40 can be freely rotated about the first axis 82 and simultaneously the stereoscopic base defined by the arrangement of the objectives 42 and the image sensors 44 can be freely rotated about the second axis 84. Both power and control signals can be provided to the image sensors 44 and image signals can be received from the image sensors 44 in any angular position of the image sensor unit 40 and in any angular position of the stereoscopic base.

In the example shown in FIG. 7, the distal end region 24 of the shaft is bifurcated. As an alternative, the distal end region can be embodied similar to the example described above with reference to FIG. 6.

Figure 8:
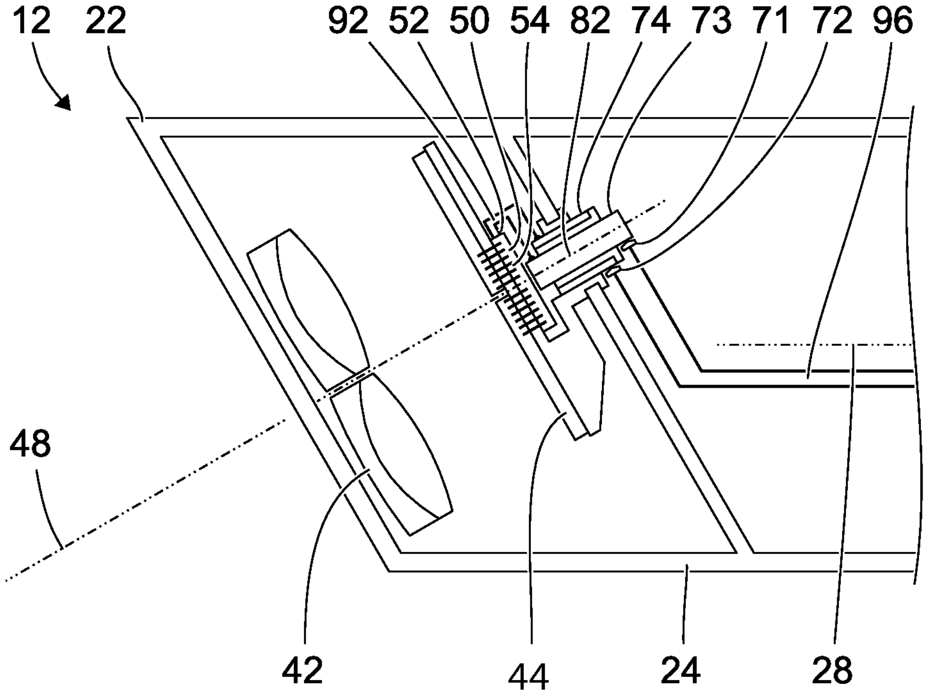
FIG. 8 shows a schematic representation of another distal end region.

FIG. 8 shows a schematic representation of the distal end 12 of another endoscope similar to the endoscopes described above with reference to FIGS. 1 through 7 with respect to many features, characteristics and functions. Differences between the distal end 12 shown in FIG. 8 and the distal ends described above with reference to FIGS. 4 through 7 are described below.

The endoscope the distal end 12 of which is shown in FIG. 8 comprises two objectives 42 and two image sensors 44 providing for stereoscopic imaging. The arrangement formed by the objectives 42 and the image sensors 44 and, thus, the stereoscopic base, can be rotated about an axis 82 parallel to the viewing direction 48. A pair of conductors 92 and an at least partially coaxial arrangement of first, second, third and fourth sliding contacts 71, 72, 73, 74 similar to the arrangements of sliding contacts described above with reference to FIGS. 4 through 7 provide a two-conductor connection between the two-conductor first interface 52 of the serializer 50 and a pair of conductors 96 running along the shaft 20 in any angular position of the stereoscopic base.

The endoscope the distal end 12 of which is shown in FIG. 8 provides a predetermined non-zero angle between the viewing direction 48 and the longitudinal axis 28 of the distal end region 24 of the shaft 20.

The endoscope the distal end 12 of which is shown in FIG. 8 has no image sensor unit distinguishable from the shaft 20. Rather, the objectives 42, the image sensors 44 and the serializer 50 are integrated into the (non-bifurcated) distal end region 24 of the shaft 20.

While the endoscope the distal end 12 of which is shown in FIG. 8 provides stereoscopic imaging, the endoscope can be provided and configured for monocular imaging as well.

While the endoscope the distal end of which is shown in FIG. 8 provides a rotation of the objectives 42 and the image sensors 44 about an axis 82 parallel to the viewing direction 48, the axis 82 and the viewing direction 48 may alternatively enclose the non-zero angle.

While the endoscope the distal end 12 of which is shown in FIG. 8 provides a predetermined angle between the viewing direction 48 and the longitudinal axis 28 of the distal end region 24 of the shaft 20, this angle can be variable as well, for example similar to the example described above with reference to FIG. 7 comprising a second at least partially coaxial arrangement of sliding contacts.

While the medical scopes described above with reference to FIGS. 1 through 8 are endoscopes, the present invention can be applied to exoscopes or surgical microscopes as well.

Although the invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

LIST OF REFERENCE NUMERALS

10 endoscope
12 distal end of the endoscope 10
14 proximal end of the endoscope 10
16 connector at the proximal end 14 of the endoscope 10
18 camera control unit in the proximal end 14 of the endoscope 10 or coupled to the connector 16
20 shaft of the endoscope 10
22 distal end of the shaft 20
24 distal end region of the shaft 20
28 longitudinal axis of the distal end region 24 of the shaft 20
30 display device
38 cable connecting the display device 30 to the camera control unit 18
40 image sensor unit at the distal end region 24 of the endoscope 20
42 objective of the image sensor unit 40
44 image sensor of the image sensor unit 40
46 flat area of the outer surface of the image sensor unit 40
48 viewing direction of the image sensor 44 and the image sensor unit 40
50 serializer in the image sensor unit 40
52 two-conductor first interface of the serializer 50
54 multi-conductor second interface of the serializer 50
60 deserializer at the proximal end 18 of the endoscope 10
62 two-conductor first interface of the deserializer 60
64 multi-conductor second interface of the deserializer 60
71 first sliding contact
72 second sliding contact
73 third sliding contact
74 fourth sliding contact
75 fifth sliding contact
76 sixth sliding contact
77 seventh sliding contact
78 eighth sliding contact
82 first axis about which the image sensor unit 40 can be pivoted and axis of symmetry of at least two of the first sliding contact 71, the second sliding contact 72, the third sliding contact 73 and the fourth sliding contact 74
84 second axis about which the image sensor unit 40 (and the first axis 82) can be rotated and axis of symmetry of at least two of the fifth sliding contact 75, the sixth sliding contact 76, the seventh sliding contact 77 and the eighth sliding contact 78
92 pair of conductors connecting the two-conductor interface 52 of the serializer 50 to first and second sliding contacts 71, 72
94 pair of conductors connecting the third and fourth sliding contacts 73, 74 or the fifth and sixth sliding contacts 75, 76 to the two-conductor interface 62 of the deserializer 60
96 pair of conductors connecting the third and fourth sliding contacts 73, 74 or the seventh and eighth sliding contacts 77, 78 to the two-conductor interface 62 of the deserializer 60

The invention claimed is:

1. A medical scope comprising:

an objective configured to produce an image of an object;

an image sensor configured to capture the image produced by the objective and to provide an image signal representing the captured image;

a serializer comprising a two-conductor first interface and a multi-conductor second interface, where the multi-conductor second interface is connected to the image sensor;

a first sliding contact and a second sliding contact, the first sliding contact connected to one conductor of the two-conductor first interface of the serializer and the second sliding contact connected to the other conductor of the two-conductor first interface of the serializer;

a third sliding contact in electrically conductive contact to the first sliding contact; and a fourth sliding contact in electrically conductive contact to the second sliding contact, wherein at least two of the first sliding contact, the second sliding contact, the third sliding contact and the fourth sliding contact are coaxial.

2. The medical scope of claim 1, further comprising:

a connector at a proximal end of the medical scope, connectable to a cable configured to electrically connect the two-conductor first interface of the serializer to a two-conductor first interface of a deserializer, the deserializer further comprising a multi-conductor second interface and being an element of a camera control unit.

3. The medical scope of claim 2, wherein the third sliding contact is coupled to one conductor of the two-conductor first interface of the serializer and the fourth sliding contact is coupled to the other conductor of the two-conductor first interface of the deserializer, and wherein the first sliding contact is in electrically conductive contact to the third sliding contact and the second sliding contact is in electrically conductive contact to the fourth sliding contact.

4. The medical scope of claim 3, wherein the serializer and the deserializer comply with the CSI Camera Serial Interface specification of the MIPI Mobile Industry Processor Interface Alliance as of the date of filing of this patent application.

5. The medical scope of claim 2, wherein the serializer and the deserializer comply with the CSI Camera Serial Interface specification of the MIPI Mobile Industry Processor Interface Alliance as of the date of filing of this patent application.

6. The medical scope of claim 1, further comprising:

an image sensor unit comprising the image sensor, the serializer, the first sliding contact and the second sliding contact; and a shaft with a distal end region including the third sliding contact and the fourth sliding contact.

7. The medical scope of claim 6, wherein the first sliding contact and the second sliding contact are part of a first coaxial plug connector, the third sliding contact and the fourth sliding contact are part of a second coaxial plug connector complementary to the first coaxial plug connector.

8. The medical scope of claim 5, wherein an axis of symmetry of the coaxial sliding contacts is parallel to the viewing direction of the image sensor unit.

9. The medical scope of claim 8, wherein the axis of symmetry of the coaxial sliding contacts is orthogonal to the viewing direction of the image sensor unit and orthogonal to the longitudinal axis of the distal end region of the shaft.

10. The medical scope of claim 9, further comprising:

a fifth sliding contact connected to the third sliding contact and a sixth sliding contact connected to the fourth sliding contact; and a seventh sliding contact in electrically conductive contact to the fifth sliding contact and an eighth sliding contact in electrically conductive contact to the sixth sliding contact, wherein at least two of the fifth sliding contact, the sixth sliding contact, the seventh sliding contact and the eighth sliding contact are coaxial.

11. The medical scope of claim 10, wherein an axis of symmetry of at least two of the first sliding contact, the second sliding contact, the third sliding contact and the fourth sliding contact and an axis of symmetry of at least two of the fifth sliding contact, the sixth sliding contact, the seventh sliding contact and the eighth sliding contact enclose an angle greater than zero.

* * * * *